US009345232B2

(12) United States Patent
Chapin et al.

(10) Patent No.: US 9,345,232 B2
(45) Date of Patent: May 24, 2016

(54) METHOD AND APPARATUS FOR TELEOPERATION, GUIDANCE AND ODOR DETECTION TRAINING OF A FREELY ROAMING ANIMAL THROUGH BRAIN STIMULATION

(71) Applicant: The Research Foundation for The State University of New York, Albany, NY (US)

(72) Inventors: John K. Chapin, Atlantic Beach, NY (US); Timothy L. Hanson, Tuxedo Park, NY (US); Linda Hermer, Gainesville, FL (US); Raymond Vazquez, Gainesville, FL (US)

(73) Assignee: The Research Foundation for The State University of New York, Albany, NY (US)

(*) Notice: Subject to any disclaimer, the term of this patent is extended or adjusted under 35 U.S.C. 154(b) by 0 days.

(21) Appl. No.: 13/667,377

(22) Filed: Nov. 2, 2012

(65) Prior Publication Data

US 2013/0098310 A1    Apr. 25, 2013

Related U.S. Application Data

(63) Continuation of application No. 11/547,932, filed as application No. PCT/US2005/011658 on Apr. 6, 2005, now abandoned.

(60) Provisional application No. 60/559,793, filed on Apr. 6, 2004, provisional application No. 60/582,652, filed on Jun. 24, 2004.

(51) Int. Cl.
*A61N 1/36* (2006.01)
*A01K 15/02* (2006.01)
(Continued)

(52) U.S. Cl.
CPC .............. *A01K 15/02* (2013.01); *A01K 1/031* (2013.01); *A61N 1/0529* (2013.01);
(Continued)

(58) Field of Classification Search
CPC   A61N 1/0529; A61N 1/36003; A61N 1/3605
USPC ........................................................... 607/48
See application file for complete search history.

(56) References Cited

U.S. PATENT DOCUMENTS

| 6,283,220 | B1 | 9/2001 | Carter |
| 6,382,070 | B1 | 5/2002 | Garcia et al. |
| 7,970,476 | B2 * | 6/2011 | Chapin et al. .................. 607/48 |
| 2002/0010390 | A1 * | 1/2002 | Guice et al. .................. 600/300 |
| 2002/0046713 | A1 * | 4/2002 | Otto ............................ 119/720 |

FOREIGN PATENT DOCUMENTS

WO    WO 03/066158 A2    8/2003

OTHER PUBLICATIONS

Talwar S.K. et al., "Rat Navigation Guided by Remote Control", *Nature* 417(NR 6884):37-38 (2002).
(Continued)

*Primary Examiner* — Eric D. Bertram
(74) *Attorney, Agent, or Firm* — Scully, Scott, Murphy & Presser, P.C.

(57) ABSTRACT

Electronic components, including a transceiver (220) for two-way wireless communications, are carried by a freely roaming animal (190) such as a rat. Electrodes are implanted in the brain of the animal to provide cues and rewards to the animal to achieved desired behaviors, including controlling the direction and speed of movement of the animal, and training the animal to recognize odors. Network interface components (265) allow a network of the animals to work together. Sensors (225, 230, 235, 245, 255, 260) carried by the animal provide information to a remote base station regarding, e.g., heading and location. Chemical or gas sensors, along with a video camera and a microphone provide information regarding an environment of the animal. The animal can search for people buried in rubble piles, and detect explosives, chemicals or other dangerous materials. A vehicle (500) for deploying the animal is also provided.

7 Claims, 4 Drawing Sheets

(51) Int. Cl.
    *A61N 1/05*      (2006.01)
    *A01K 1/03*      (2006.01)
    *A61N 1/372*     (2006.01)
    *G06N 3/06*      (2006.01)
    *B62D 63/02*     (2006.01)
    *F41H 11/132*    (2011.01)

(52) U.S. Cl.
    CPC ......... *A61N 1/36003* (2013.01); *A61N 1/3605* (2013.01); *A61N 1/36025* (2013.01); *A61N 1/37282* (2013.01); *B62D 63/02* (2013.01); *F41H 11/132* (2013.01); *G06N 3/061* (2013.01); *A61N 1/36017* (2013.01); *A61N 1/36082* (2013.01)

(56) References Cited

OTHER PUBLICATIONS

Xu S. et al., "A Multi-Channel Telemetry System for Brain Microstimulation in Freely Roaming Animals", *Journal of Neuroscience Methods* 133(NR 1-2):57-63 (2004).
Supplementary Partial European Search Report dated Feb. 26, 2008 from related European Patent Application 05778398.7.
U.S. Office Action dated Aug. 31, 2011 from parent U.S. Appl. No. 11/547,932.
U.S. Final Office Action dated May 2, 2012 from parent U.S. Appl. No. 11/547,932.

* cited by examiner

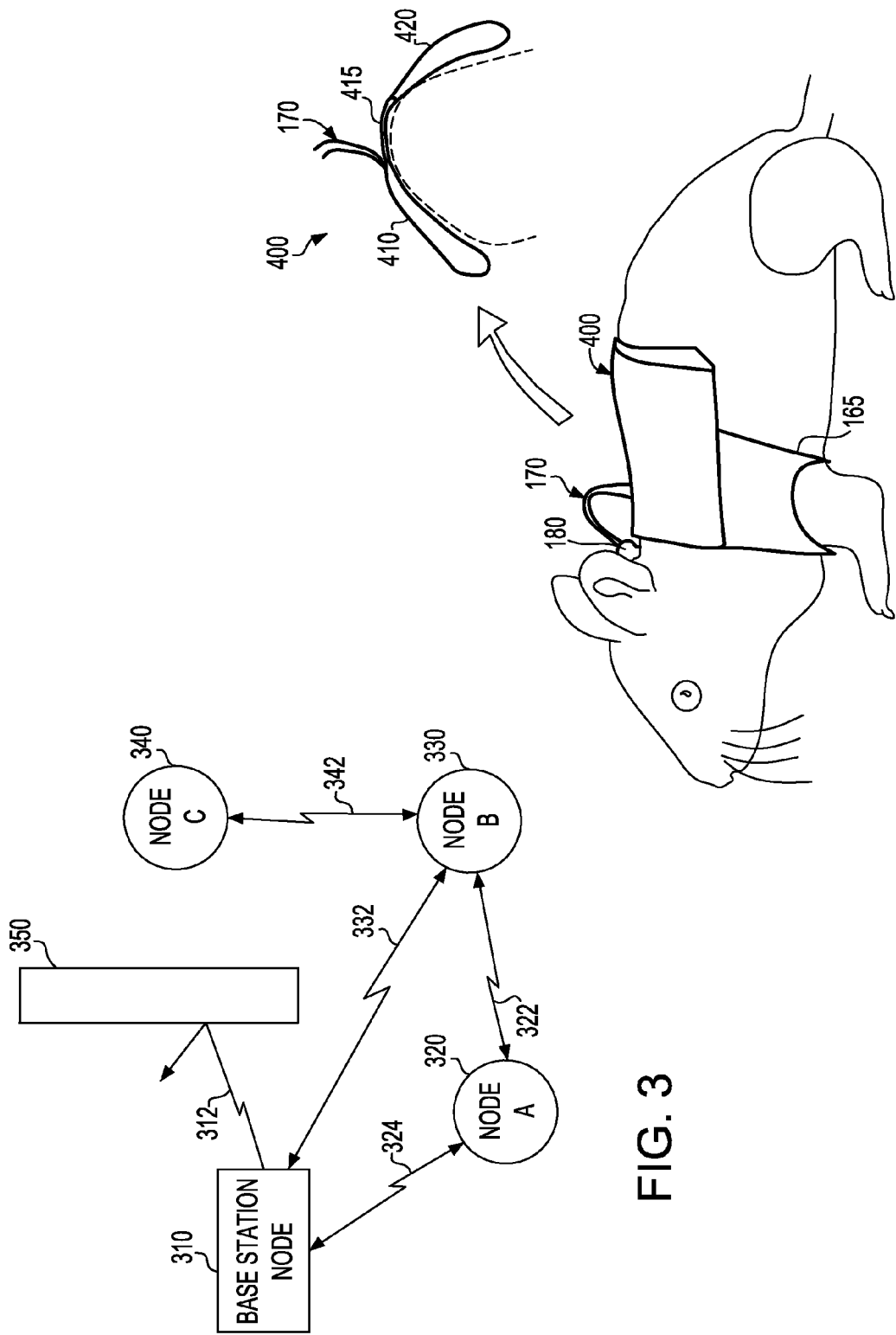

METHOD AND APPARATUS FOR TELEOPERATION, GUIDANCE AND ODOR DETECTION TRAINING OF A FREELY ROAMING ANIMAL THROUGH BRAIN STIMULATION

CROSS REFERENCE TO RELATED APPLICATIONS

This is a continuation of U.S. patent application, Ser. No. 11/547,932, filed Oct. 20, 2008, which is a 371 of International Application No. PCT/US2005/011658 filed Apr. 6, 2005, which claims benefit from U.S. provisional patent application, Ser. Nos. 60/559,793, filed Apr. 6, 2004 and 60/582,652, filed Jun. 24, 2004, the contents of all of which are incorporated herein by reference.

BACKGROUND OF THE INVENTION

1. Field of Invention

The invention relates generally to the field of guiding the movement of animals and, more specifically, to a method and apparatus for guiding the movement of a freely roaming animal using electric stimulation of the animal's brain, where the capabilities of the remotely guided animals are enhanced through teleoperation, guidance and odor detection training.

2. Description of Related Art

Existing technologies mainly involve use of unmanned vehicles to penetrate remote spaces. Remotely guided animals are far superior in their ability to locomote through difficult terrain. Unlike robots, they do not quickly run out of battery power.

Moreover, animals are superior to robots because they possess native abilities that allow them to autonomously find sensory targets, including odors and other environmental features.

Techniques for guiding the movement of a freely roaming animal through brain stimulation have been discussed in the above-mentioned U.S. patent application publication no. 2003/0199944. Such remotely guided animals can penetrate small, dangerous and otherwise inaccessible spaces to map them, return sensor information and carry out simple tasks. The animals are instrumented with electronic communication devices and sensors, and are guided using remote brain stimulation.

However, it would be desirable to enhance the capabilities of the remotely guided animals through teleoperation, guidance and odor detection training.

BRIEF SUMMARY OF THE INVENTION

The present invention addresses the above and other issues by providing a method and apparatus for teleoperation, guidance and odor detection training of a freely roaming animal through brain stimulation.

Advantageously, a remotely guided animal that is trained to search for target odors can autonomously carry electronic sensors into inaccessible or dangerous spaces to carry out a variety of missions, including searching for people buried in rubble piles, law enforcement operations, and detection of explosives, chemicals or other dangerous materials. The enhancements disclosed herein markedly increase the capability of this technology.

In one aspect, the invention provides an apparatus for use by a freely roaming animal that includes a control for controlling movement of the animal by controlling energizing of electrodes that are implanted in the animal's brain, sensors associated with the control for providing data, and a transceiver associated with the control for receiving a wireless control signal from a remote operator for controlling the movement of the animal, and for transmitting a wireless signal carrying the data.

In another aspect, a network of freely roaming animals includes a plurality of network interface devices and associated transceivers, where each network interface device hosts a node of the network, and each network interface device and transceiver is carried by a respective one of the animals, and a base station network interface device and transceiver, where the base station network interface device hosts a base station node of the network.

In yet another aspect, a method for training a freely roaming animal includes monitoring the animal's behavior, and controlling movement of the animal by remotely controlling the energizing of electrodes that are implanted in the animal's brain to achieve a desired behavior.

In yet another aspect, a method for training a freely roaming animal to detect a target odor includes recording olfactory recognition signals from the animal's brain, and responsive to the recording, analyzing the olfactory recognition signals to determine whether there is a recognition event indicating that the animal has detected the target odor.

In a still further aspect, a remotely controlled propelled vehicle for deploying an animal includes means for carrying an animal, means for egressing the animal from the carrying means; and means for receiving wireless control signals for controlling the vehicle and the egressing means.

BRIEF DESCRIPTION OF THE DRAWINGS

These and other features, benefits and advantages of the present invention will become apparent by reference to the following text and figures, with like reference numbers referring to like structures across the views, wherein:

FIG. 3 illustrates a network of remotely controlled animals according to the invention;

FIG. 4 illustrates a saddlebag style backpack for use by a remotely controlled animal according to the invention;

FIG. 5b illustrates a bottom view of the remotely controlled land-going vehicle of FIG. 5a.

DETAILED DESCRIPTION OF THE INVENTION

Figure 1:
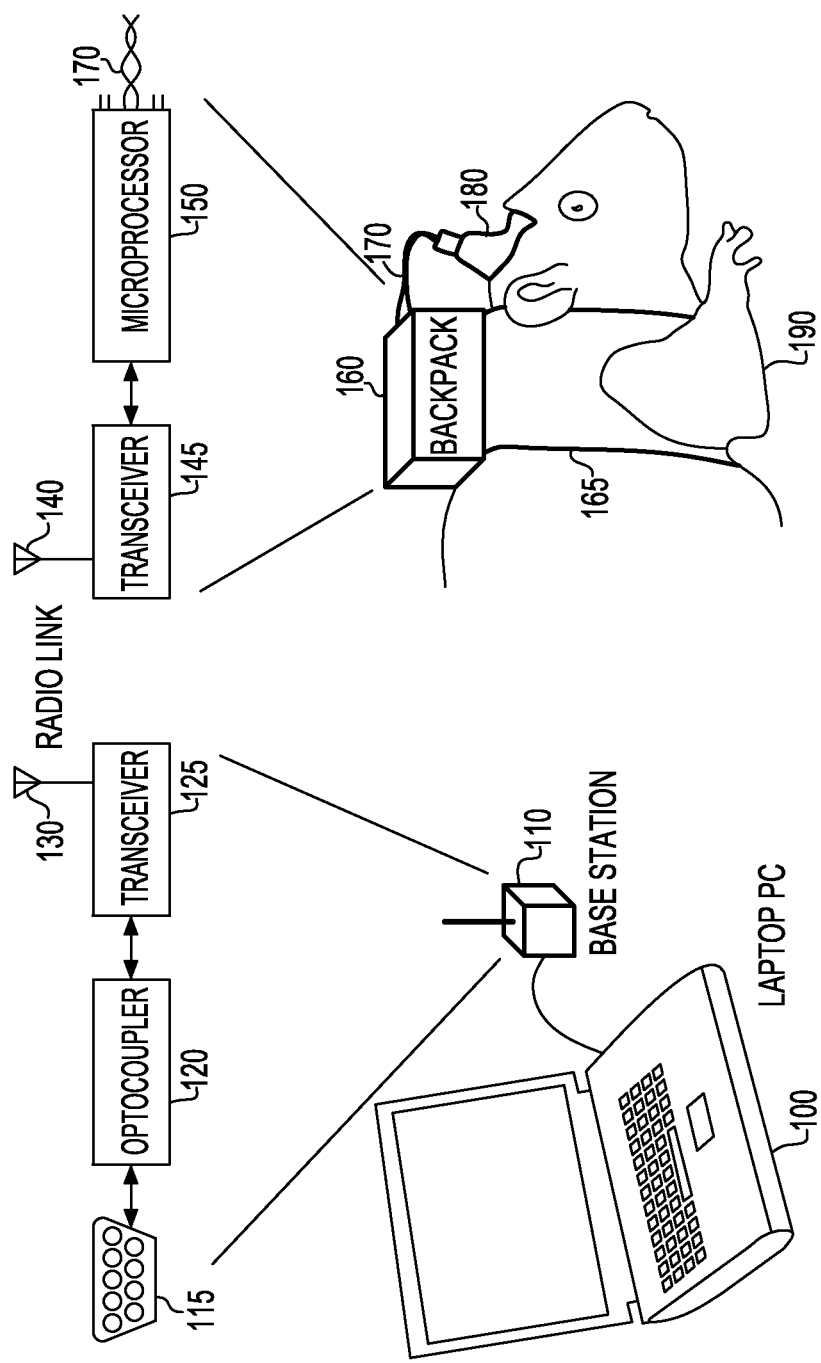
FIG. 1 illustrates an overview of a system for controlling an animal by remote control, according to the invention.

FIG. 1 illustrates an overview of a multichannnel tele-stimulation system showing the main components of the system and the signal flow. In one possible approach, a laptop personal computer 100 receives commands from an operator, e.g., via specific keystrokes, for guiding movement of a freely roaming animal 190, such as a rat. The laptop 100 sends a control signal to a base station 110 via a serial RS232 port 115. The term "base station" is meant to encompass any component used by an operator to remotely control the animal. An optocoupler 120 processes the signal and provides it to a transceiver (transmitter-receiver) 125, e.g., as a transistor-transistor logic (TTL) signal. The transceiver 125 transmits the signal via antenna 130 and a radio link to an antenna 140 of a transceiver 145, which is carried by the animal 190, such as in a backpack 160 that is secured to the animal using a cloth harness 165 that wraps around the neck of the animal.

One possible such backpack available from Harvard Apparatus (Holliston, Mass.) measures 48 mm×23 mm×19 mm and weighs 28 g, and is worn by the rat 190 by means of mating Velcro pieces. The harness 165 has two holes for the front legs and extends backwards over the trunk for three inches, providing a semi-stiff surface for mounting the electronic devices.

In one possible backpack design, shown in FIG. 4, the electronic backpack 400 includes first and second side portions 410, 420, such as saddlebags, in which electronic components such as circuit boards are provided. The circuit boards can be connected by a flexible interconnect circuit material 415, such as wires encased in plastic, that allows the side pieces of the backpack to hang down like saddle bags from each side of the animal's back. This design allows the rat to carry at least 100 g of payload. The side portions 410, 420 can be made of a flexible or rigid material, and can be sealed to repel water and dirt. Various other designs are possible.

Referring again to FIG. 1, the transceiver 145 provides the received TTL signal to a microprocessor 150, which, in turn, controls electrodes that are implanted in the animal's brain. A skull-top adapter 180 on the animal can house the electrodes, although other approaches can be used for connecting electrodes to the brain. A battery or other energizing means can be housed in the backpack 160, which sends electrical current, via short wires 170, to the electrodes to energize the electrodes to provide the desired stimulations to the brain sites to which the electrodes are attached. Note that more than two electrodes can be used. In one possible design, sixteen electrodes are used. In practice, a pair of wires and electrodes is used for each brain site to be stimulated. Note that the configuration shown is merely one possible example, which has been found to be convenient for use by researchers. The particular remote control set-up can be adapted to particular applications. Moreover, additional components can be carried by the backpack 160 or otherwise secured to the animal 190, including an upstream transmitter, e.g., in the transceiver 145, for communicating video, audio, and/or other data back to the operator via the transceiver 125 on the base station side. Other data, such as data regarding the position and orientation of the animal, can also be communicated upstream to the base station, as discussed further below.

Depending on the site of brain stimulation, an electric stimulus can act as a cue and/or reward. Moreover, a reward stimulus can act as a cue as well. While studies investigating such phenomena have generally been concerned with functional mechanisms of the nervous system, little thought has been given to the potential of behavioral paradigms constructed wholly around such focal brain stimulations. The present inventors employed stimulation of a reward center of the brain to provide cues for moving forward, and stimulation of portions of the brain that control left and right movement as cues for moving left or right, respectively. For example, the reward center can include the medial forebrain bundle (MFB), ventral tegmental area, or other regions of the lateral hypothalamus. The portion of the brain for controlling left and right movement can include the primary somatosensory (SI) areas of the brain, such as cortical representations of left and right whiskers of the animal. In a particular experiment, SI and MFB stimulations, which act as virtual cues and rewards, respectively, were delivered to freely roaming rats. Behavioral contingencies were imposed so that an operator could accurately steer the animal, in real-time, over any arbitrarily specified 3-dimensional route and over any real-world terrain.

Stimulating electrodes were implanted in the MFB, plus right and left SI whisker representations of a number of rats. The whisker representations mimic the rat's sensation of being lightly touched on the face. For example, if the rat has the sensation of being touched on the right side of the face, e.g., as if the rat was contacting a barrier on its right side, it will turn to the left to avoid the barrier. Similarly, a sensation on the left side of the face results in a right turn. The backpack 160, containing a microprocessor-based remote-controlled microstimulator, was then mounted on each animal. This allowed the operator using the laptop computer 100 to directly deliver brief trains of 80 μA stimulus pulses to any of the implanted brain-sites at distances up to 500 meters (typically ten, 0.5 msec, biphasic pulses at 100 Hz). Training the rats to navigate took ten sessions, during which the animals learned to interpret remotely received brain stimulation as instructions for directing their trajectory of locomotion. In a figure-8 maze, they first learned to obtain periodic MFB rewards (0.3-3 Hz) by running forward and turning correctly whenever left or right turning cues were issued; these cues were presented as "touch" stimulation of the left or right whiskers by stimulating their respective cortical representations. The animals were then placed in open environments that lacked the rectilinear structure and fixed choice points of the maze. All rats generalized their responses to their new environments, running forward and turning instantaneously on cue. They moved at speeds averaging 0.3 m/s and worked continuously for periods up to a 1-hour test limit.

Figure 2:
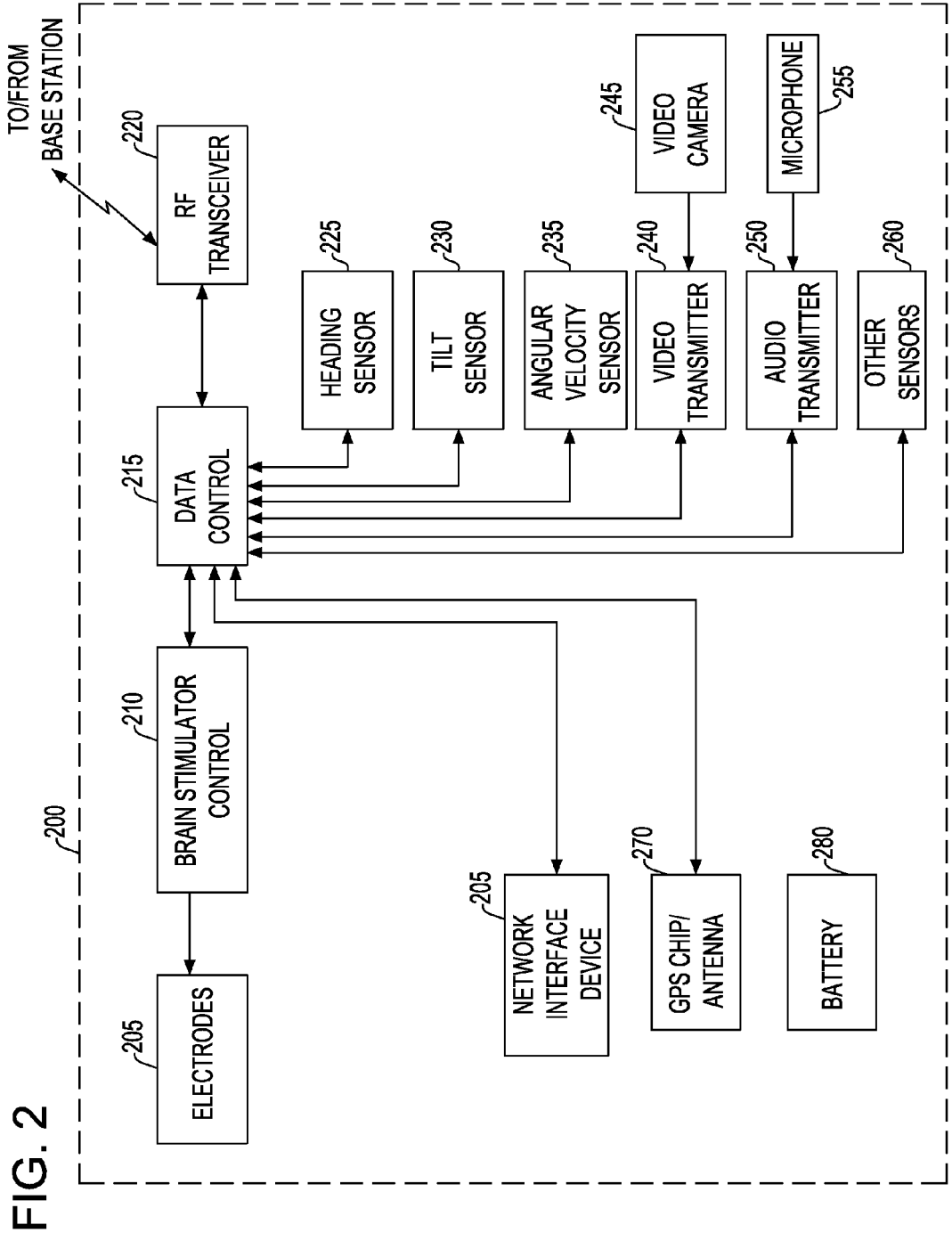
FIG. 2 illustrated components carried by a remotely controlled animal, according to the invention.

FIG. 2 illustrated components carried by a remotely controlled animal, according to the invention. The enhancements provided by the present invention include a new assemblage of communication and sensor electronics that are integrated on the animal backpack 160 or other location on or about the animal. The electronic components, shown generally at 200, can include various control and sensing components that improve the ability of the operator to remotely control and track the animal's progress, and obtain data regarding the environment in which the animal travels. In one possible approach, bi-directional communication with the operator is provided using a digital RF transceiver 220 (available from MaxStream, Inc., Orem, Utah), which communicates with the base station, e.g., using serial data communication A microcontroller data control 215 is used for general control functions on the backpack, such as supervising data communication. The data control 215 can be a microcontroller chip such as a BASIC Stamp chip (Parallax, Inc.) or PIC chip (Microchip Technology Inc.). The BASIC Stamp chip is a tiny single-board computer with 16 I/O lines, built around a microcontroller, that runs a version of BASIC. Its 2 Kbyte EEPROM holds the executable program and any data. Its 32 bytes of RAM serve as variable space and I/O pin interface for the BASIC program. The PIC 16/17 microcontrollers are low-cost 8-bit CMOS devices that incorporate a CPU, (E)PROM, RAM, and I/O. The data control 215 communicates with a brain stimulation control 210, such as a 16-channel microcontroller, to relay commands from the operator for controlling the animal via the electrodes 205. The data control 215 also receives and sends digital data via the transceiver 220.

The data control 215 can also communicate with various sensors and transmitters such as to gather data from them and organize the transmission of this data back to the base station 110 via the transceiver 220. The data control 215 receives data from the base teleoperator, e.g., the remote human operator, and uses it to control the backpack electronic devices, particularly to present trains of stimuli through up to sixteen electrodes implanted in the brain. The sensors and transmitters can include a heading sensor 225, a title sensor 230, an angular velocity sensor 235, a video transmitter 240 responsive to at least one video camera 245, an audio transmitter 250 responsive to at least one microphone 255, and other sensors 260, e.g., temperature sensors, water sensors, radioactivity sensors, sensors that detect various gases such as toxic gases, sensors that detect chemicals, and so forth. A network interface device 265 can be provided to give the animal a networking capability, as described in connection with FIG. 3. A global positing system (GPS) component 270, such as a chip and antenna, can be provided to monitor the location of the animal. A battery 280 provides power to the various components, e.g., using a lithium battery pack, charge pumps and connecting wires.

By implementing a full duplex wireless interface to the backpack, two-way communication with the guided animals is realized, and the operator's ability to guide the animal through remote spaces is greatly enhanced. In a test, a backpack digital transceiver was implemented that can transmit and receive digital data at line of sight distances up to seven miles. Baud rates of, e.g., 37 Kbaud or higher, are sufficient for handling all backpack communication functions. The transceiver 220 receives signals from the teleoperator, including queries as to the state of the electronics on the backpack, controls for the backpack sensor and control electronics, and guidance specifications for the brain stimulator control 210. The transceiver 220 sends signals back to the teleoperator, including responses to queries and controls, and data from sensor electronics on the backpack.

Moreover, teleoperation is enhanced by providing sensor data to the operator. For example, the heading sensor 225, title sensor 230 and angular velocity sensor 235 provide information regarding the animal's movements and orientation to further assist the teleoperator in guiding the rat through a 3D space. The heading sensor 225 can be implemented by an electronic compass, such as the Honeywell Model HMC6352 two-axis electronic compass. The tilt sensor 230 can be implemented by a two-axis accelerometer tilt sensor and/or a 3-axis gyroscope, which can be used to increase its accuracy in determining heading direction when video signals are noisy or unavailable. The angular velocity sensor 235 can be implemented by a three-axis gyroscope. The data provided to the base station by the sensors 225, 230 and 235 allows the animal's movements to be mapped even when video signals are noisy or unavailable. Moreover, the compass can be of the type that is tilt compensated and resists magnetic interference, so that it normally yields a good heading direction. One type provides heading direction at a maximum rate of 20 Hz. When these sensors 225, 230 and 235 are used together, they provide important information to the teleoperator about the animal's heading direction and postural pitch. However, information from one or more of the sensors is still useful if less than all sensors are available or functioning.

Development of an on-back navigation system for the remotely guided animal provides a further advantage. In tests, a single chip GPS system 270 (Motorola Oncore™) was implemented on the backpack to provide global position data accurate to within 5-10 meters. Power consumption can be kept relatively low by selecting a GPS system that can go into sleep mode when not taking a reading. In use, the GPS antenna receives wireless signals from synchronized satellites that indicate their respective locations and transmission times. The distance to each satellite is estimated based on the amount of time it takes for their signals to reach the GPS receiver. The GPS receiver can then calculate its position. The position can be calculated in three dimensions when signals from at least four satellites are received.

The GPS receiver communicates with the data control 215 to send data back to the base station that indicates the animal's current position.

The electronic compass and GPS system send data through the digital transceiver 220 to the base station, providing valuable information to the teleoperator about the animal's heading direction and location. In particular, teleoperation and semi-autonomous guidance can be provided using backpack heading and position sensors. For example, the animal can be semi-autonomously guided by the data control 215 using the compass and/or GPS system for feedback. The teleoperator need only specify a heading direction and/or a target location, and the data control 215 can carry out the guidance autonomously by providing appropriate cues and rewards to the animal's brain. For example, the teleoperator can specify a target location, e.g., in terms of a longitude and latitude. The data control 215 can be programmed with software for recognizing the animal's current location using data from the GPS, and plotting a course to the target location. The course can be plotted as a straight line, for example. Or, if the data control 215 is programmed with information regarding geographic features such as obstacles, e.g., roads and waterways, an appropriate course can be plotted to avoid the obstacles.

Generally, the usefulness of the guided animal can be improved by miniaturizing the backpack electronics. Regarding the battery 280, for example, a set of polymer lithium-ion batteries that each provides about 300 mAh of power at 3.7 V, in a flat 8 g package, can be used. To provide increased power to the electronic components 200, a number of the batteries, e.g., three, can be arranged in the saddlebags 410, 420 (FIG. 4). This will provide up to three hours of continuous power to the transceiver 220, data control 215, video camera 240 and video transmitter 245 (using about 80 mA), for example (FIG. 2).

Regarding the video camera 245, different types of color or monochrome video cameras can be implemented to address different needs. In one approach, a tiny video camera that is only 9 mm square and 16 mm long, weighs under 30 g, and can be mounted on the rat's backpack, for instance. The lumbar area of the back is a suitable location since it is the most stable part of the body. The video camera can also be mounted on the head, which experiences less rotational movement than the backpack. This camera has good (380 lines) resolution and low (0.5 lux) sensitivity. The camera can thus use a high shutter speed, even in dim light, preventing smearing of the video images. It only consumes 20 mA power at 12 V. In another approach, a camera with a wide-angle lens (2.5 mm, 105 degree field of view) can be implemented. This wide-angle view substantially reduces the shaking that is visible in narrower frames, and which is caused by movements of the animal, and thus increases the ability of a teleoperator to guide the animal through unknown spaces. The video transmitter 245 can be a miniature transmitter weighing under 10 g, which sends the video camera output back to the base station, where it is viewed by the teleoperator.

On the base station side, to improve reception of the wireless video, audio and/or other data transmissions for teleoperation, multiple directional gain antennas can be used. For example, up to four active directional and/or omni-directional antennas can be placed in appropriate locations, and wired to the inputs of a 4-channel diversity receiver which automatically determines which of the four antennas is receiving the best signal. This allows the video signal to be monitored as the animal moves through different spaces, and also reduces interference due to multi-path reflection. This approach has proved invaluable in both indoor and outdoor tests. As constituted, this system provides real-time video feedback sufficient to allow a teleoperator to guide the animal through remote spaces.

A computer-based system can be used to further stabilize the video images transmitted from the animal. In one approach, video signals (composite 60 frames/sec. or fps) received from the animal are digitized and processed by a video graphics processor that functions as a front-end to a computer workstation. Software algorithms are used to measure the rotation and the translation of each video frame relative to the previous frame. Based on this error measurement, each frame is overlaid onto a video mosaic, which renders a stabilized composite image of the scene traversed by the camera in real-time. In the video mosaic, video frames with partially differing views of a scene are registered and rendered as a single larger image on a computer screen.

FIG. 3 illustrates an ad hoc network of multiple animal sensor nodes 320, 330 and 340, and a base station node 310, according to the invention. A digital wireless communication network can be used to control and monitor the movements of each of a number of remotely guided animals. In one approach, an ad hoc wireless digital network running the IEEE 802.11 wireless Ethernet format can be used. However, any networking technique known to the ordinarily skilled artisan can be used. Each animal carries a small network interface device 265 (FIG. 2) such as a network interface card/chip that can host a single node of the ad hoc network. Similarly, the base station 310 includes a base station network interface device. An address such as an IP address can be associated with each network interface device 265 and therefore with each animal and the base station. Information can be routed in "multi-hop" mode through multiple nodes, allowing the teleoperator to obtain appropriate sensor information from any or all of the animal sensors.

This network can also transmit packetized digital messages through transmission links extending into spaces that are otherwise unreachable with single-hop wireless signals. For example, a barrier 350 prevents the base station node from communicating directly with node C (340), as indicated by communication path 312. The barrier 350 can be a man made barrier such as a wall or building, or a natural barrier such as a hill or rock formation. In this case, communications between the base station node and node C (340) can be achieved via one or more other nodes in the network, such as node B (330) and/or node A (320), which are able to communicate with both the base station node 310 and node C (340). For instance, the base station node 310 can communicate directly with node A (320) via path 324, or directly with node B (330) via path 332. Node B (330) can communicate with node A (320) via path 322, and with node C (340) via path 342. Essentially, the data meant to be exchanged between nodes that cannot communicate directly, such as the base station node 310 and node C (340), can be relayed through one or more other nodes.

Moreover, the transmission of data by one of the animals can be coordinated with position data of the animal, such as data obtained from the heading sensor 225. Also, images from digital video cameras carried by the animals can be transmitted through the network at a rate consistent with the bandwidth of the network interface chips. For instance, images from digital video cameras on the heads of each of the animals could be sampled at a slow rate, e.g., once per second or every few seconds, similar to the approach used in many CCTV surveillance systems, to avoid consuming bandwidth unnecessarily. The video images can be streamed, for instance. Or, the video images can be grabbed only at a particular time, such as when the animal is pointed in a particular direction, as measured using an electronic compass on the animal. This approach results in fewer frames being provided to the teleoperator, while ensuring that the frames carry important information. For example, the operator can wish to obtain images only when the camera carried by the animal is aimed in a particular direction, e.g., north, east, south or west. Moreover, the same approach could be used to transmit a wide variety of data between the animals and the operator, including movement instructions from the operator to each animal. These instructions can command direct movements of the animal. Alternatively, the instructions can direct the backpack microcontroller to control movements autonomously, using the backpack compass and other devices for navigation. For example, high-level instructions can be handled by the on-animal processors through local navigational methods.

With a network of remotely guided animals, it is valuable to train and guide the animals for specialized tasks. "Seekers" are animals that are trained to use olfactory and other senses to find a particular kind of target, e.g. people in the rubble, explosives, and drugs. The seekers carry a camera and a low power wireless communication system. They transmit the visual and other sensor data at low power to nearby followers who will re-transmit this data at higher power through the network. "Followers" are animals that are trained to closely follow their designated seekers everywhere. The followers can receive low power, high bandwidth (e.g., uncompressed) signals from their seeker, process the signals, including performing compression, and then transmit the compressed signals through the network at higher power. The followers' purpose can be to off-load power and weight from the seekers by carrying the electronic circuits for performing specific tasks. For example, a seeker can carry a video camera but not a GPS device, while its follower carries a GPS device, which helps to locate the seeker as well as the follower.

"Relays" are animals that form a chain of repeaters, e.g., networks devices used to regenerate or replicate a signal, to ensure the connectivity between the seeker/follower and the base station. Their purpose can be to help relay the sensor information from the seekers back to the base station, rather than to search for desired targets. The controllers in their backpacks help to guide them to stay a proper distance from their neighbors and regain connectivity once lost, with minimal guidance from the base station.

The transceiver of each animal can encode the signals it transmits according to an identifier of the animal so that the source of a signal can be identified. Similarly, signals intended for receipt by the transceivers of one or more specific animals can be encoded according to those animals' identifiers. Also, the identifiers can be unique to each animal, or can specify a type or category of animal, e.g., seeker, follower, relay, of which there can be one or more animals of each type or in each category.

Furthermore, stationary mechanical relays can be jettisoned by the remotely-guided animals or put in place by other means. From the network perspective, it is not necessary to distinguish between a seeker and its follower, but rather to consider the pair as one node.

Techniques for training the remotely guided animals comprise further aspects of the invention. In particular, the present invention provides methods for training animals for direct and semi-autonomous guidance, animal sensor networks and odor detection.

In a first training aspect, three techniques for inducing the animals to run at faster or slower speeds are as follows. First, the rate of MFB stimulation can be varied in proportion to a desired running speed of the animal, since one highly robust effect of this stimulation is to directly enhance locomotion speed. A higher rate results in a faster speed. Second, the animal can be directly conditioned to run at a fast pace between known fixed locations. Third, variable ratio reinforcement, involving providing a reward for traveling a random distance, produces the fastest overall running speed.

In a second training aspect, the backpack electronics and animal training are used to maintain animal sensor network connectivity. Specifically, various techniques can be used to ensure that animals are properly positioned to maintain network connectivity. A first technique is to reward animals for maintaining their connectivity with other animals. In this approach, the backpack microcontroller, e.g., data control 215, periodically rewards the animals for maintaining wireless connections with other relays. Each animal's transceiver 220 periodically broadcasts an identification signal at relatively low output power. When these signals are received by other animals' backpacks, they respond, allowing both animals to be rewarded. As long as both connections are being maintained, the animals remain in the appropriate position. When the seeker animals move, all the relay animals should be trained/guided to move in a cooperative manner to maintain a target signal strength between neighbors.

A second technique for maintaining network connectivity is to train the animals for behavioral strategies to find lost connectivity. That is, the animals are trained to behaviorally recover or improve their connections. This involves reinforcing behaviors that they do well without training, e.g., when they suddenly stop receiving a reward they "scan" the area to recover it. First, they revisit recently rewarded locations, and then they randomly search the whole area before quitting. The animals can be reinforced for performing these connectivity searches more diligently and for employing particular strategies, such as going to high ground.

A third technique for maintaining network connectivity is to semi-autonomously guide the animals to regain connectivity by optimizing signal strength from multiple connections. When an animal cannot find the correct position, it is moved to the correct position using semi-autonomous guidance. To determine which direction to go, the transceivers measure gradients in strength of signals from other nodes. The transceivers normally operate at the lowest power necessary to maintain transmission/reception. If signal is lost, the power is increased in successive increments until the connection is restored. As the animal moves around spontaneously, or by direction of the semi-autonomous program, it defines a spatial map of the signal strength gradient. Maintenance of connections with multiple animals thus involves finding the location that optimizes the signal strength from each animal connection.

In a third training aspect, the animals are trained to actively search for odorants in real-world areas. In particular, the use of MFB stimulation techniques for odor search reinforcement is superior to food reward for reinforcing odor detection performance. The present inventors have demonstrated that the MFB stimulation technique provides the ideal reinforcement for training animals to find and discriminate different odors in a maze. Since this is a much stronger reward than food, the animals generally move faster to the odor target and dig more energetically. The advantage with this virtual reward system is that animals can be remotely guided to the general location of an odor target, and then can be remotely rewarded when they find the target.

The animals can be trained to detect odor targets by first training the animals to find a food object, which can be hidden above ground or in sawdust. The food is associated with a neutral target odor as a reinforced conditional stimulus (CS+), such that after a few trials the animal will work to find the CS+ alone, as long as it is rewarded with food or MFB stimulation. In the most proficient animals, the MFB-CS+ association is very long-lasting. For example, after a six-week hiatus in which no further behavioral training or testing took place, these animals still homed in on the odor and dug for it in the correct location in <30 sec/trial. These animals also disregard distractions such as non-reinforced conditional stimulus (CS−) odors, e.g. digging only for a specific individual's odors and bypassing odors of other individuals.

Generalization training can be used in which the animals learn to perform the odor-hunting task despite changes in the arena's geometry, the lighting of the room, or the presence of various distractor odors. These animals can be rewarded with MFB stimulation at random temporal intervals to keep them motivated to perform the task. This is particularly important when animals are searching for the CS+ in large environments.

In a fourth training aspect, olfactory recognition signals from the animal's brain during olfactory discrimination can be recorded. In particular, electrical recordings (neural recordings) in the brains of animals can be used to detect the animals' recognition of a target odor. These neural signals are recorded as field potentials and multineuron activity patterns in the animal olfactory cortex and other brain regions. In a well-controlled, olfactory-driven GO/NO-GO reaching task, the inventors determined that, upon CS+ recognition, a sharp depression of spike firing and a membrane hyperpolarization occurred in the posterior piriform cortex, as well as the primary motor cortex and red nucleus. This recognition event was also detected using field potentials as a brief (~40 ms) high-gamma oscillation in these areas. A mathematical method can be used for combining the olfactory information obtained using multi-single neuron recordings and field potentials to obtain a combined function that predicts olfactory recognition with high accuracy, e.g., 84%.

Similar neural signals are also found during more naturalistic odor hunting, such as food-deprived animals that detect a buried chocolate chip and dig for it. Detection of these signals therefore allows the teleoperator to determine when an animal searching for odors in a complex environment has detected a target odor, without requiring an explicit conditioned response. When combined with an explicit conditioned response, the overall reliability of olfactory detection increases still further.

Various other training techniques can be provided using the apparatus and method of the invention.

Figure 5A:
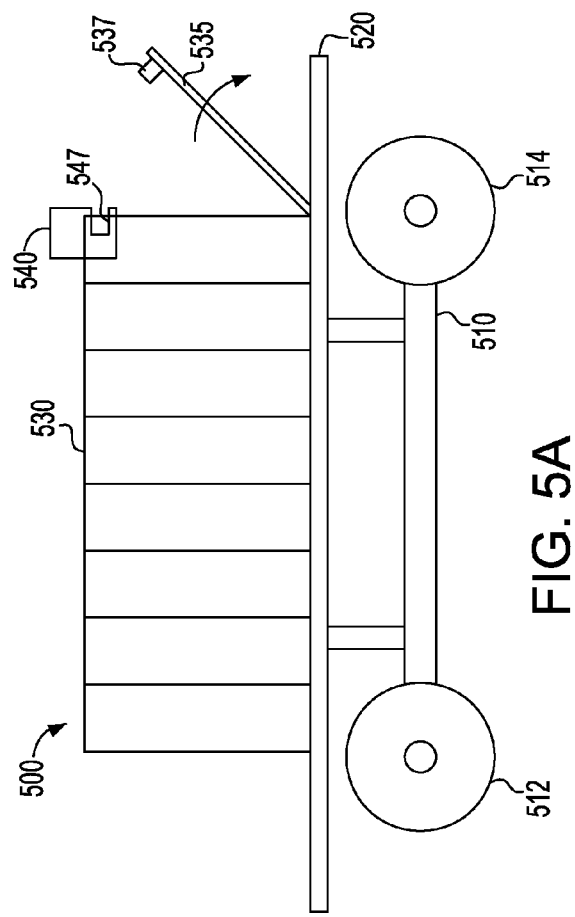
FIG. 5a illustrates a remotely controlled land-going vehicle for deploying a remotely controlled animal.

FIG. 5a illustrates a remotely controlled land-going vehicle for deploying a remotely controlled animal. The remotely controlled animal discussed above can be more easily deployed to a desired location by a robotic vehicle. In one approach, a propelled land-going vehicle is used. However, propelled sea-going and air going vehicles can be used as well. Moreover, the same vehicle may be able to traverse land, sea, and/or air. The example land-going vehicle 500 is a wheeled robot that is remotely controlled by the operator. The vehicle 500 can have wheels and/or treads similar to those used on a tank or otherwise adapted to a specified terrain. The wheels can be designed for travel on and/or off road. For example, at least two wheels, including wheels 512 and 514, can be provided. A frame 510 supports the wheels and a platform 520 on which a cage 530 is provided. A door 535 of the cage swings down to allow the animal to enter the cage 530, or egress from the cage 530. The door 535 includes a member 537 that can be engaged in an opening 547 of a locking mechanism 540.

Figure 5B:
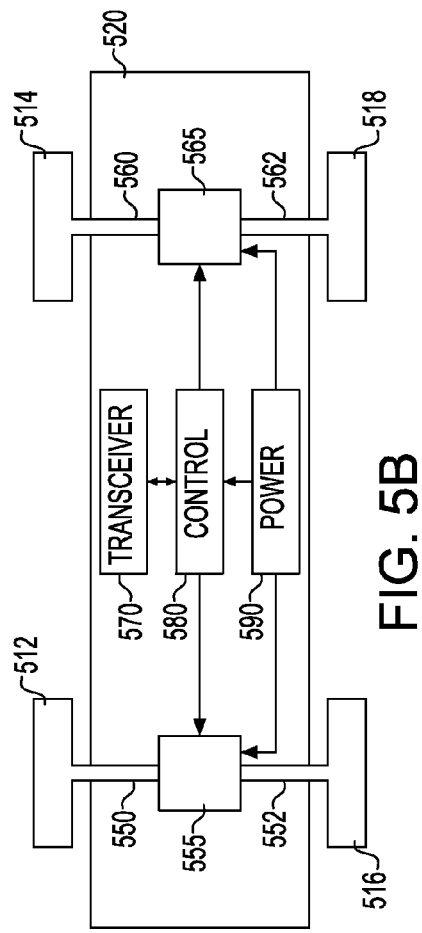

FIG. 5b illustrates a bottom view of the remotely controlled land-going vehicle of FIG. 5a. A motor 550 powers rear wheels 512 and 516 via axles 550 and 552, respectively, while an additional motor 565 controls steering of the front wheels 514 and 518 via axles 560 and 562, respectively. The motor 565 can also power the front wheels 514 and 518. A transceiver 570 receives wireless control signals from the operator for controlling the vehicle 500 and the locking mechanism 540 via a control 580. The control 580 controls propulsion and steering via motors 555 and/or 565. An on-board power source 590 powers the control 580 and motors 555 and 565. The control can transmit information back to the operator via the transceiver 570 regarding, e.g., status information of the vehicle such as faults detected, remaining battery life and so forth. The components used for controlling the vehicle 500 can be analogous to those used for remotely-controlled toy cars.

In use, the vehicle can be used to transport an animal such as a sniffing rat to another location. When the location is reached, the rat is deployed by sending a control signal to open the door 535 to allow the rat to egress from the cage 530 to perform its mission. In an example mission, the rat is remotely guided to a nearby area which, contains samples of different odors, such as explosive chemicals such as RDX and TNT. The rat can detect these odor targets, and then be guided back into the robot vehicle 500, which is then controlled to return the rat to the operator's location or another location.

Moreover, the transceiver 570, or an additional transceiver, can be used for communicating with the deployed animal, such as after it egresses from the vehicle. In an example scenario, the teleoperator can release the rat or other animal by remotely opening the door 535 of the cage 530. The rat walks out of the cage and then is guided through the area searching for odors or other targets. The rat's backpack 160 sends wireless signals, e.g., from a video camera, compass, gyro, GPS component, biosensor, brain, etc., to the transceiver 570 on the robot, and this signal is then sent wirelessly back to a base station. The signal can be relayed to the base station, for instance. In one possible approach, two different repeater systems are used to transmit signals to the base station: one analog video and the other digital. Similarly, the base station can transmit signals to the transceiver 570 which are, in turn, relayed or to the transceiver carried b the animal.

The robot is advantageous because it can carry a relatively large, heavy battery that provides power to handle sending and receiving wireless signals over longer distances than would be possible by a smaller battery carried by the animal. The robot is also advantageous for use in dangerous or otherwise inaccessible environments.

The invention has been described herein with reference to particular exemplary embodiments. Certain alterations and modifications will be apparent to those skilled in the art, without departing from the scope of the invention. The exemplary embodiments are meant to be illustrative, not limiting of the scope of the invention, which is defined by the appended claims.

The invention claimed is:

1. A network of freely roaming animals, comprising:
a plurality of network interface devices and associated transceivers;
wherein each network interface device hosts a node of the network, and each network interface device and transceiver is carried by a respective one of the animals;
the transceiver of a first of the animals receives a wireless signal from a base station, and relays the wireless signal to a second of the animals, wherein the transceiver of each of the animals is configured to encode the wireless signal with an identifier of the animal, and wherein, the wireless signal controls movement of the second animal by controlling energizing of electrodes that are implanted in the second animal's brain, wherein the transceiver of each of the animals is configured to encode the wireless signal with a category identifier of the animal, and wherein the category identifier of the animal is selected from the group consisting of seeker, follower and relay.

2. The network of claim 1, wherein:
a base station network interface device hosts a base station node of the network.

3. The network of claim 2, wherein:
the transceiver of a first of the animals receives a wireless signal which is transmitted by the transceiver of at least a second of the animals and relays the wireless signal to the base station node.

4. The network of claim 3, wherein:
the wireless signal carries data from a sensor carried by the second animal.

5. The network of claim 1, wherein:
the freely roaming animals include at least one seeker animal.

6. The network of claim 1, wherein:
the freely roaming animals include at least one follower animal that follows at least one seeker animal.

7. The network of claim 1, wherein:
the freely roaming animals include at least one relay animal for relaying data from a seeker and/or follower animal.

* * * * *